US00PP16955P2

(12) United States Plant Patent
Dümmen

(10) Patent No.: US PP16,955 P2
(45) Date of Patent: Aug. 8, 2006

(54) ***GERANIUM* PLANT NAMED 'DUEBERTINOSTAR'**

(50) Latin Name: *Pelargonium peltatum*
Varietal Denomination: Duebertinostar

(75) Inventor: Marga Dümmen, Rheinberg (DE)

(73) Assignee: Dümmen Jungpflanzen GbR, Rheinberg (DE)

( * ) Notice: Subject to any disclaimer, the term of this patent is extended or adjusted under 35 U.S.C. 154(b) by 0 days.

(21) Appl. No.: 11/171,912

(22) Filed: Jun. 30, 2005

(51) Int. Cl.
*A01H 5/00* (2006.01)

(52) U.S. Cl. ..... Plt./332
(58) Field of Classification Search ..... Plt./332
See application file for complete search history.

*Primary Examiner*—Kent Bell
(74) *Attorney, Agent, or Firm*—C. A. Whealy

(57) ABSTRACT

A new and distinct cultivar of Ivy *Geranium* plant named 'Duebertinostar', characterized by its compact, upright and outwardly spreading plant habit; freely basal branching habit; freely flowering habit; and light red and light pink bi-colored double flowers.

1 Drawing Sheet

Botanical denomination: *Pelargonium peltatum.*
Cultivar designation: 'Duebertinostar'.

BACKGROUND OF THE INVENTION

The present invention relates to a new and distinct cultivar of Ivy *Geranium* plant, botanically known as *Pelargonium peltatum,* and hereinafter referred to by the name 'Duebertinostar'.

The new Ivy *Geranium* is a product of a planned breeding program conducted by the Inventor in Rheinberg, Germany. The objective of the breeding program was to develop new compact and freely-flowering Ivy *Geraniums* with attractive flower and foliage colors.

The new Ivy *Geranium* is a naturally-occurring whole plant mutation of a proprietary selection of *Pelargonium peltatum* identified as code number E-02-05, not patented. The cultivar Duebertinostar was discovered and selected by the Inventor as a flowering plant within a population of plants of the parent selection in a controlled environment in Rheinberg, Germany in May, 2003.

Asexual reproduction of the new cultivar by terminal vegetative cuttings at Rheinberg, Germany since May, 2003 has shown that the unique features of this new Ivy *Geranium* are stable and reproduced true to type in successive generations of asexual reproduction.

SUMMARY OF THE INVENTION

The following traits have been repeatedly observed and are determined to be the unique characteristics of 'Duebertinostar'. These characteristics in combination distinguish 'Duebertinostar' as a new cultivar and distinguish it from the other known Ivy *Geranium* cultivars:

1. Upright and outwardly spreading plant habit.
2. Freely basal branching habit.
3. Freely flowering habit.
4. Light red and light pink bi-colored double flowers.

Plants of the new Ivy *Geranium* differ primarily from plants of the parent selection in flower color as plants of the parent selection have light red-colored flowers.

The new Ivy *Geranium* can be compared to plants of the cultivar Duebertino, disclosed in U.S. Plant Pat. No. 15,751. In side-by-side comparisons conducted in Rheinberg, Germany, plants of the new Ivy *Geranium* differed from plants of the cultivar Duebertino in the following characteristics:

1. Plants of the new Ivy *Geranium* were shorter but broader than plants of the cultivar Duebertino.
2. Plants of the new Ivy *Geranium* had larger leaves with longer petioles than plants of the cultivar Duebertino.
3. Plants of the new Ivy *Geranium* had larger flowers than plants of the cultivar Duebertino.
4. Plants of the new Ivy *Geranium* and the cultivar Duebertino differed in flower coloration as plants of the cultivar Duebertino had light red-colored flowers.

BRIEF DESCRIPTION OF THE PHOTOGRAPH

The accompanying colored photograph illustrates the overall appearance of the new cultivar, showing the colors as true as it is reasonably possible to obtain in colored reproductions of this type. Flower and foliage colors in the photograph may differ slightly from the color values cited in the detailed botanical description which accurately describe the colors of the new Ivy *Geranium*. The photograph comprises a side perspective view of a typical flowering plant of 'Duebertinostar' grown in a container.

DETAILED BOTANICAL DESCRIPTION

The cultivar Duebertinostar has not been observed under all possible environmental conditions. The phenotype may vary somewhat with variations in environment, such as temperature and light intensity, without, however, any variance in genotype.

The aforementioned photograph, following observations and measurements describe plants grown in Rheinberg, Germany during the summer under commercial practice in a glass-covered greenhouse with day and night temperatures about 18° C. and light levels about 4,500 foot-candles. Plants were grown in 10.5 cm containers. Plants were pinched about three weeks after planting. Plants were about eight weeks from unrooted cuttings when the photograph and the detailed botanical description were taken.

In the following description, color references are made to The Royal Horticultural Society Colour Chart, 1995 edition, except where general terms of ordinary dictionary significance are used.

Botanical classification: *Pelargonium peltatum* cultivar Duebertinostar.

Parentage: Naturally-occurring whole plant mutation of a proprietary selection of *Pelargonium peltatum* identified as code number E-02-05, not patented.

Propagation:

*Type cutting.*—Terminal vegetative cuttings.

*Time to initiate roots.*—Summer: About 5 days at 20° C. Winter: About 7 days at 20° C.

*Time to develop roots.*—Summer: About three weeks at 20° C. Winter: About four weeks at 20° C.

*Root description.*—Fine; fibrous; white in color.

*Rooting habit.*—Freely branching.

Plant description:

*General appearance.*—Upright and outwardly spreading plant habit, rounded plant form; densely foliated.

*Growth and branching habit.*—Moderately vigorous. Freely basal branching, about five lateral branches per plant.

*Plant height.*—About 23 cm.

*Plant width.*—About 15 cm.

*Lateral branches.*—Length: About 25 cm. Internode length: About 3.7 cm. Texture: Smooth. Color: 144A.

*Foliage description.*—Arrangement: Alternate, single. Length: About 6.5 cm. Width: About 7.8 cm. Shape: Reniform. Apex: Acute. Base: Peltate. Margin: Crenate. Venation pattern: Palmate. Texture, upper and lower surfaces: Smooth, glabrous. Color: Developing and fully expanded foliage, upper surface: 137A; zonation pattern, faint, 147A in color and about 6 mm in width. Developing and fully expanded foliage, lower surface: 137C. Venation, upper surface: 144A. Venation, lower surface: 144B. Petiole: Length: About 4.4 cm. Diameter: About 2 mm. Color, upper and lower surfaces: 144A.

Flower description:

*Flower arrangement.*—Light red and light pink bi-colored double flowers arranged in rounded hemispherical umbels arising from apical leaf axils. Umbels displayed above the foliage on upright peduncles. Flowers rounded in form. Umbels persistent, flowers not persistent. Flowers not fragrant.

*Quantity of flowers.*—Freely flowering; plants have about seven open umbels with about eight to nine flowers per umbel.

*Flowering season.*—Flowering continuous spring through summer.

*Flower longevity.*—Flowers last about five to seven days on the plant.

*Umbel size.*—Diameter: About 7.5 cm. Height: About 5 cm.

*Flower size.*—Diameter: About 4.9 cm. Depth (height): About 2 cm.

*Flower buds.*—Length: About 1.25 cm. Diameter: About 6.3 mm. Shape: Ovoid. Color: 144A.

*Petals.*—Quantity per flower: About five. Length: About 2.9 cm. Width: About 1.7 cm. Shape: Obovate. Apex: Rounded. Base: Attenuate. Margin: Sinuate. Texture, upper and lower surfaces: Smooth. Color: When opening and fully opened, upper surface: Center, 69D; towards the margin and longitudinal stripes, 46B; towards the base, 60C to 60D; color towards the margin and longitudinal stripes becoming closer to 46C with development. When opening and fully opened, lower surface: Center, 69D; towards the margin and longitudinal stripes, 46D.

*Petaloids.*—Quantity per flower: About four to six. Length: About 2.6 cm. Width: About 1.7 cm. Shape: Obovate. Apex: Rounded. Base: Attenuate. Margin: Sinuate. Texture, upper and lower surfaces: Smooth. Color: When opening and fully opened, upper surface: Center, 69D; towards the margin and longitudinal stripes, 46B. When opening and fully opened, lower surface: Center, 69D; towards the margin and longitudinal stripes, 46B.

*Sepals.*—Quantity per flower: About five or six, arranged in a single whorl. Length: About 1.1 cm. Width: About 3 mm. Shape: Elongated, tapering. Apex: Apiculate. Margin: Entire. Texture, upper and lower surfaces: Smooth, glabrous. Color, upper and lower surfaces: 144A to 144B.

*Peduncle* (*umbel stem*).—Length: About 11.8 cm. Diameter: About 1 cm. Angle: Erect. Strength: Moderately strong. Texture: Smooth, glabrous. Color: 144A.

*Pedicel* (*individual flower stem*).—Length: About 2 cm. Diameter: About 2 mm. Angle: Erect. Strength: Moderately strong. Texture: Pubescent. Color: 144A.

*Reproductive organs.*—Androecium: Anther quantity per flower: About seven to eight. Anther length: About 3 mm. Anther shape: Ovate. Anther color: 47C. Pollen amount: Moderate. Pollen color: 28A. Gynoecium: Pistil quantity per flower: One. Pistil length: About 1 cm. Stigma shape: Crested. Stigma color: 46A to 46B. Style length: About 3 mm. Style color: 2D. Ovary color: Close to 144A.

*Seed/fruit.*—Development of seeds and fruit have not been observed.

Disease/pest resistance: Plants of the new Ivy *Geranium* have not been observed to be resistant to pathogens and pests common to Ivy *Geraniums*.

Temperature tolerance: Plants of the new Ivy *Geranium* have been observed to be tolerant to temperatures ranging from 5° to 40° C.

It is claimed:

1. A new and distinct cultivar of Ivy *Geranium* plant named 'Duebertinostar', as herein illustrated and described.

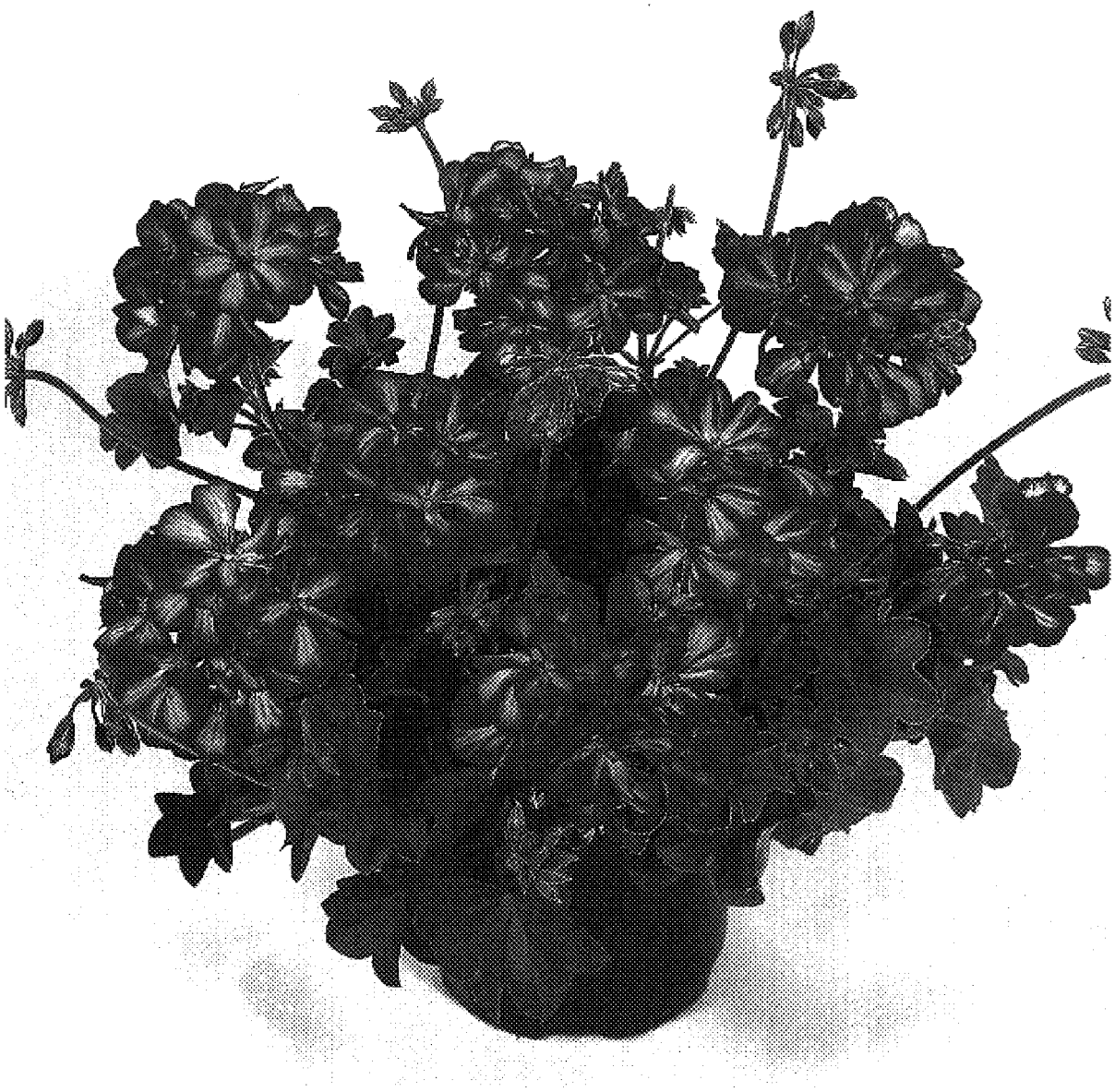

* * * * *